United States Patent [19]
Krajíček

[11] Patent Number: 5,968,089
[45] Date of Patent: Oct. 19, 1999

[54] INTERNAL SHIELD OF AN ANASTOMOSIS IN A VASCULAR SYSTEM

[76] Inventor: Milan Krajíček, 140 00 Praha 4,5. května 19, Prague, Czech Rep.

[21] Appl. No.: 08/915,423

[22] Filed: Aug. 20, 1997

[30] Foreign Application Priority Data

Aug. 21, 1996 [CZ] Czech Rep. ............................ 2461-96

[51] Int. Cl.[6] .................................................. A61F 2/06
[52] U.S. Cl. ................... 623/1; 623/12; 623/11; 606/153; 600/36
[58] Field of Search .............................. 623/1, 12; 604/8; 606/153, 158, 144, 148, 194, 233, 228, 216

[56] References Cited

U.S. PATENT DOCUMENTS

| | | | |
|---|---|---|---|
| 4,368,736 | 1/1983 | Kaster | 128/344 C |
| 4,503,568 | 3/1985 | Madras | 3/1.4 |
| 4,938,740 | 7/1990 | Melbin | 606/153 X |
| 5,197,976 | 3/1993 | Herweck et al. | 623/1 |
| 5,643,340 | 7/1997 | Nunokawa | 623/1 |

*Primary Examiner*—Mickey Yu
*Assistant Examiner*—Alvin Stewart
*Attorney, Agent, or Firm*—Akin, Gump, Strauss, Hauer & Feld, L.L.P.

[57] ABSTRACT

A device, whose purpose is such internal shielding of a vascular anastomosis that undesirable perivascular vibration is avoided, is created from a stiff or possibly moderately elastic, non-resorbable, biologically inert, non-moistenable and sterilizable material. The shield has the form of an incomplete tube (4), whose length is at least five times larger than the diameter of the targeted vessel or substitute. This incomplete tube (4) in the third and fourth fifths of its length (counting counter to the course of blood flow) is provided with an orifice (5) having a width of at least one quarter of the circumference of the tube. From the apical end of the orifice (5) and/or from the rear end of the said orifice (5) projects a gradually tapered tongue-shaped structure (6, 10) which is moderately bow-curved externally. The margin (8) of the orifice (5) and all margins of the device are blunt, and the whole internal surface of the device is highly polished.

18 Claims, 3 Drawing Sheets

INTERNAL SHIELD OF AN ANASTOMOSIS IN A VASCULAR SYSTEM

BACKGROUND OF THE INVENTION

The internal shield of an anastomosis in accordance with the invention solves the problem of the origin of so-called intimo-medial hyperplasia, which quite often develops in an anastomosis in a vascular system, particularly in the case of vascular reconstructions of smaller caliber, and leads to a resulting occlusion of the reconstruction.

The anastomosis in the vascular system is basically an artificially created connection either of actual vessels or of an actual vessel and a biological or artificial arterial substitute vessel, and most commonly is executed by suturing with the use of a special suturing material. Such anastomosis can be created in any part of the vascular system regardless of its caliber. In most cases, the connection from end to side is desirable or preferred.

In the case of anastomoses in small caliber areas, which generally means diameters up to 6 mm ( for example the reconstruction of coronary arteries ), there exists a certain problem, occurring relatively often after some time period, usually after several months, and having no dependence on the technical quality of the performed anastomosis. It is the phenomenon standardly described as intimo-medial hyperplasia. This means that in the connection, most commonly in the apex of the anastomosis, a mound gradually develops consisting of the structures of the hyperplastic intima and media of the targeted vessel, that is the vessel on which the connection is created in the direction of blood flow. The situation is best illustrated in FIG. 1., which is a schematic drawing of an anastomosis of the vessel 1 and an in-flowing vascular substitute 2, end to side. The intimo-medial hyperplasia 3 is illustrated in a typical location; and the blood flow is indicated by the arrows. This gradually growing structure 3a,3b understandably leads to the stenosis of the cross-section of the reconstruction, reduction of the blood flow, and ultimately to complete occlusion.

The generally accepted theory of the development of this phenomenon is as follows: the created anastomosis disturbs, in dependence on different circumstances, the different characteristics of blood flow, most commonly so-called stability of the flow, which is expressed by Reynolds' number. The anastomosis also disturbs the normal laminar flow toward turbulence. In a direct relation, higher turbulence also means a higher quantity of liberated energy. The forces which activate the perivascular transfer of the energy by vibration across the vascular wall are simultaneously the cause of the chronic stress and damage of the surrounding tissue, and at the same time, initiate the response of biochemical mediators, and in their ultimate effect lead to the gradual development of the intimo-medial hyperplasia At the present time, there is no known method, in the accessible literature, which could prevent this undesirable biological process with some degree of reliability. The most common preventive measure is the creation of a maximally wide anastomosis. This possibility is, of course, objectively limited by the caliber of connected tubes, either vessels or vessel and substitute.

SUMMARY OF THE INVENTION

The internal reinforcement of the created anastomosis by a stiff lining in accordance with the invention eliminates the principal cause of the intimo-medial hyperplasia, i.e., the perivascular transfer of the energy liberated by the turbulence across a soft vascular wall with permanent vibrational stress and subsequent tissue reaction.

The device in accordance with the invention comprises a semi-tubular formation having a diameter commensurate to the diameter of the targeted vessel or substitute. The semi-tubular formation is created from a stiff, lightly elastic, sterilizable, biologically inert and non-moistenable material having such a length that the most commonly affected locations are lined. In the third and fourth fifth of the length (counted counter to the direction of the blood flow) an orifice is formed on the convexity of the tube. The orifice corresponds in length to at least double the diameter of the targeted vessel and in width to at least a quarter of the circumference of this vessel. From the apex of this orifice (in the direction of the blood flow) a tongue-shaped structure arises at an angle of 20–45 degrees from the longitudinal axis and counter to the direction of blood flow. The tongue-shaped structure has a length at least twice the diameter the targeted vessel, and of such a form that it gradually spreads into margins of the orifice, so that this transition does not exceed one third the length of the orifice from the base of the tongue-shaped structure counter to the blood flow. The margins of the orifice are so formed that they moderately deviate externally at the top, as does as the tongue-shaped structure, which as a whole also moderately deviates externally. On both sides of the margin in the middle of its length as well as frontally ahead of the base of the tongue-shaped structure and in the rear behind the end of the orifice, are created pairs of small holes for fixation sutures on the targeted vessel or substitute. These holes are created in such way that these fixating sutures can be employed at sufficient distance from the margins of an open vessel, so the anastomosis can be executed distally from the orifice of the device.

In some rare cases the development of the intimo-medial hyperplasia occurs on the rear of the anastomosis (counter to the blood flow). For these cases the device is created on the same principle with the tongue-shaped structure projecting into the in-flowing vessel or substitute at the same angle, but arising from the rear end of the orifice in the device and with a gradual transition into margins of the orifice, but not exceeding one third of the length of the orifice.

By the combination of both solutions it is possible to create a double-tongued device, with one shaped structure projecting in length at least twice the diameter of the targeted vessel or substitute from the apex of the orifice of the device, and with the other tongue-shaped structure projecting from the rear end of the orifice, both tongues having the same length and projecting at the same angle of 20–45 degrees from the longitudinal.

In all cases, the material used should be non-resorbable, sterilizable, biologically inert, non-moistenable, stiff or moderately elastic, either by itself (e.g. stainless steel, carbon steel, carbon composites, glass, or synthetic materials) or in different physical or chemical combinations, most commonly in the form of coatings (e.g., stainless steel coated by graphite, synthetic base coated by titanium etc.). Further, the internal and/or external surface of the device may be equipped (e.g., coated) with a physically or chemically-bonded pharmacologically active material.

Simultaneously with securing proper structural stability, the device is as thin-walled as possible with all margins blunt.

BRIEF DESCRIPTION OF THE SEVERAL VIEWS OF THE DRAWING

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

In the drawings the same reference numerals will be used throughout to designate the same or similar elements.

DETAILED DESCRIPTION OF THE INVENTION

Figure 1:
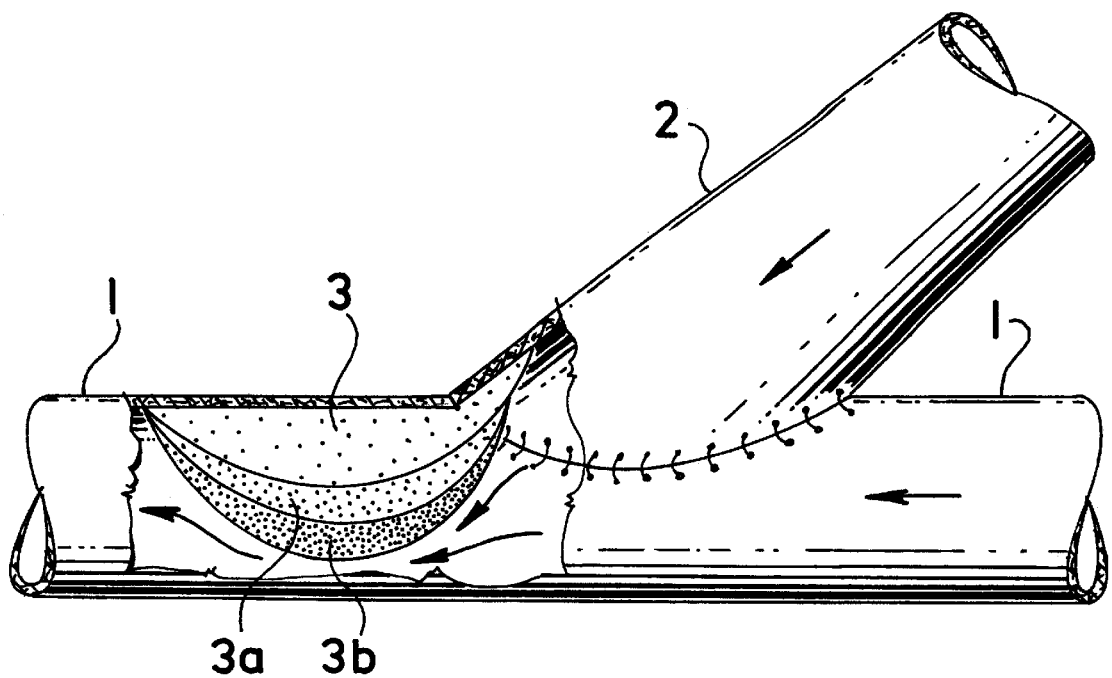
FIG. 1 schematically illustrates the typical location of intimo-medial hyperplasia.
Figure 2:
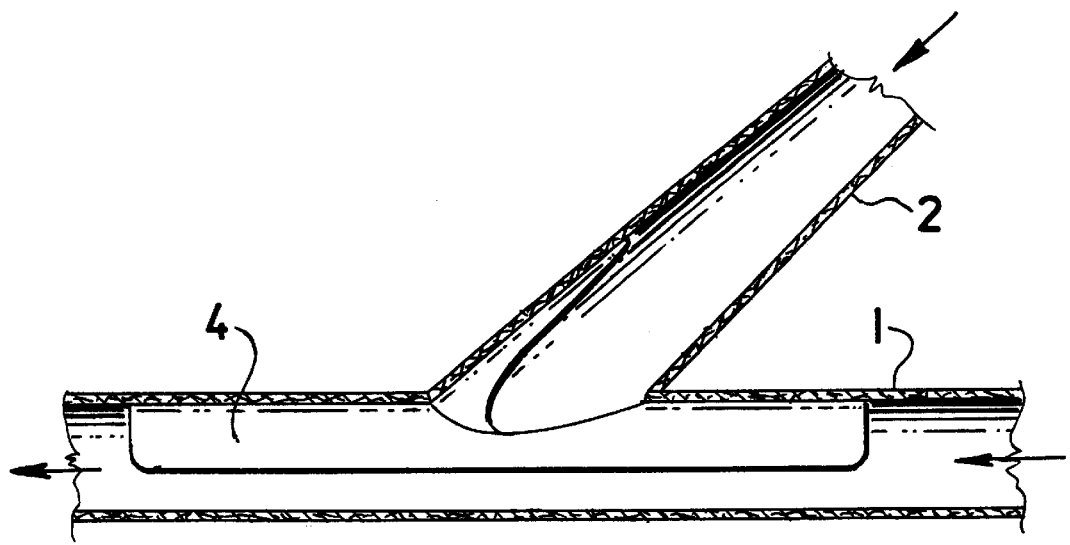
FIG. 2 schematically shows the typical location of the internal shield according to the invention in an anastomosis.
Figure 3:
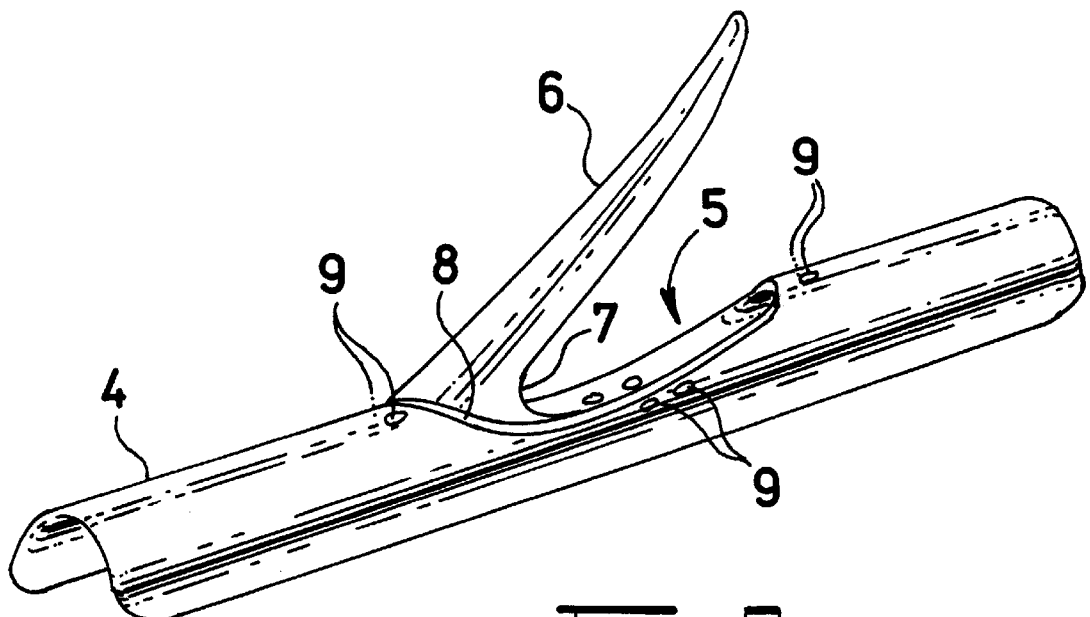
FIG. 3 illustrates the whole device of the invention with its typical characteristics.
Figure 4:
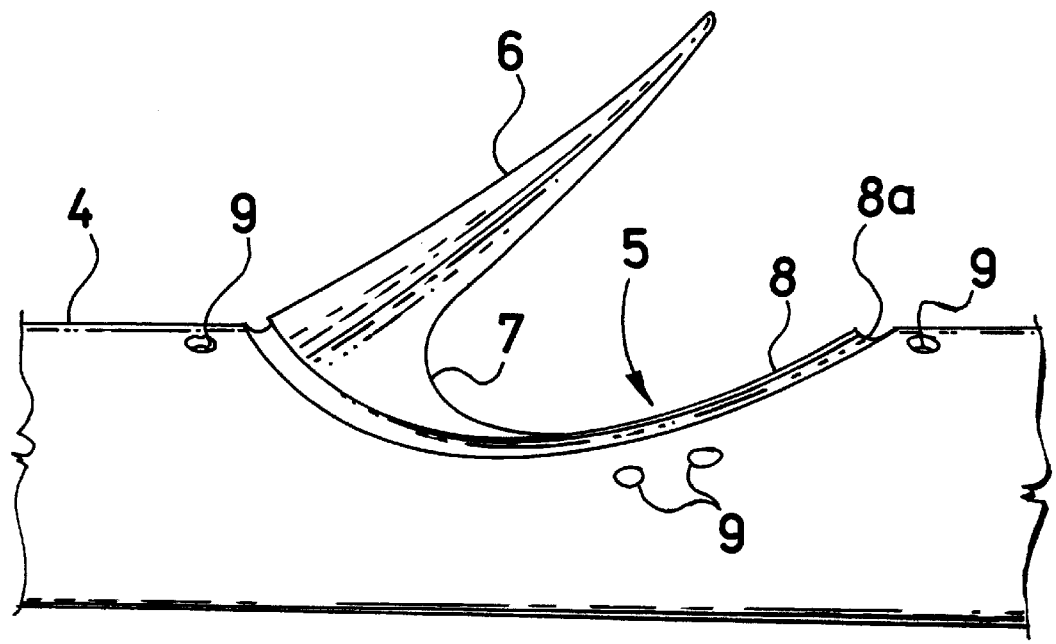
FIG. 4 illustrates the detail of the margin of the orifice and of the base of the tongue-shaped structure.
Figure 5:
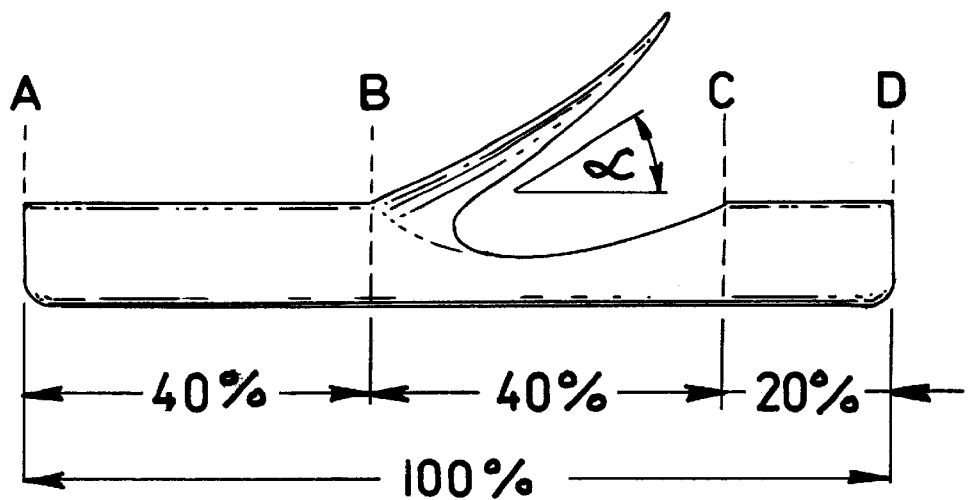
FIG. 5 illustrates the dimensional relation of individual parts of the device and the angle of projection of the tongue-shaped structure.
Figure 7:
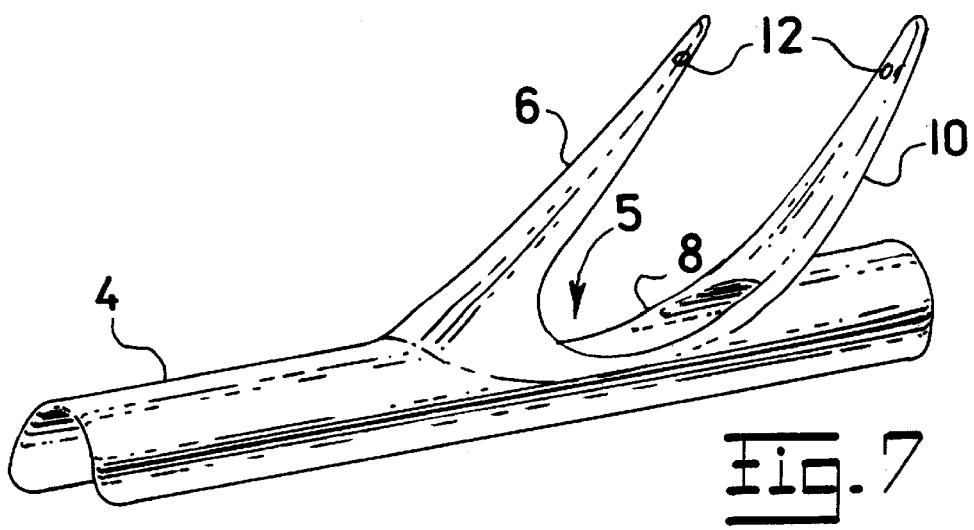
FIG. 7 illustrates the device with the tongue-shaped structures projecting from the apex as well as the rear end of the orifice.

From a thin-walled carbon steel is formed an incomplete tube 4 in the form of two thirds of the circumference of a 6 mm diameter tube. This incomplete tube forms the body 4 of the device shield (see FIGS. 2 and 3), and its entire length is at least 30 mm, where the first two fifths A–B of the length, as well as the last fifth C–D, are continuous (See FIG. 5). In the third and fourth fifth B–C on the convexity, the elliptic orifice 5 is formed, at least 5 mm wide measured on the circumference. From the apical end of this orifice 5 a tongue-shaped structure 6 projects upwardly at an angle of 20–45 degrees from the longitudinal direction of the device (see, for example, FIGS. 3, 4 and 7). The tongue-shaped structure is at least 5 mm wide at its base, moderately bow curved toward the exterior, and gradually tapered toward the tip with a minimum length in the central axis of 12 mm. This tongue-shaped structure 6 is moderately spread at its base and transitions gradually at its foot 7 into the margin 8 of the orifice 5. Outside of the margin 8 of the orifice 5 at a distance of at least 2 mm are located pairs of small holes 9 for placing the fixation sutures on the wall of the targeted vessel or substitute. The whole internal surface is highly polished and the margins are blunt.

In another embodiment of the invention (see FIG. 4), the device has all the characteristics of the above device, but the margins 8 of the orifice 5 are formed in such way that they are moderately curved externally 8a, i.e., concave, and the external surface of the base of the tongue-shaped structure 6 is curved in the same way.

Figure 6:
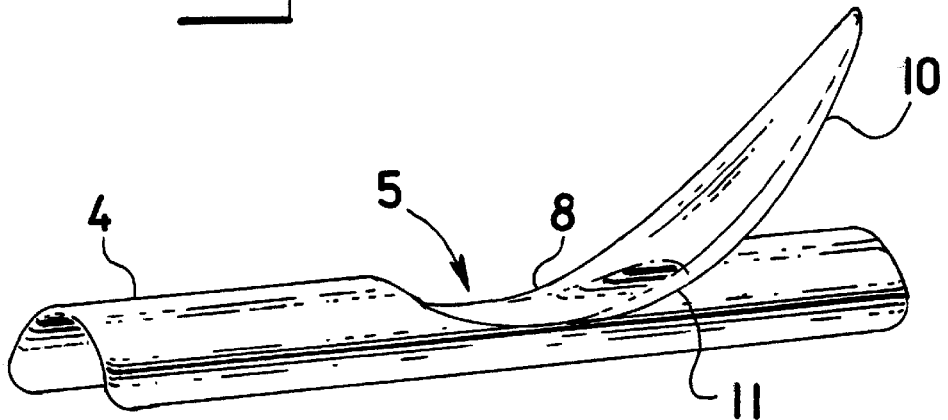
FIG. 6 illustrates the device with the tongue-shaped structure projecting from the rear end of the orifice.

In another embodiment (see FIG. 6), a device manufactured from thin-walled stainless steel has a body 4 at least 30 mm long, wherein the tongue-shaped structure 10 arises from the rear end of orifice 5 at an angle of 30 degrees and counter to the blood flow. The whole internal surface of the device is coated by a thin layer of graphite.

According to another embodiment (see FIG. 7), the device is manufactured from TEFLON®, whose body 4 is at least 30mm long. From the margin 8 of the orifice 5 one tongue-shaped structure 6 projects from the apical end (counter to the blood flow) at an angle of 30 degrees and has a length of at least 12 mm, while from the rear end of the same orifice 5 a similar tongue-shaped structure 10 projects at an identical angle and with an identical length as the tongue-shaped structure 6 of this device. The whole internal surface of the shield device is coated by a thin layer of titanium and is highly polished. The tongue-shaped structures 6 and/or 10 may have a pair of suture holes 12 for attachment to the in-flowing vessel.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A prosthetic device for internal shielding of a vascular anastomosis connected end-to-side, said device comprising
   a) an elongated thin wall, defining an incomplete tube (4) having a diameter, a length, a longitudinal axis, and front and rear ends, said wall comprising a segment of a circumference of a complete tube, the device being adapted for insertion into a blood vessel with the front end downstream and the rear end upstream of blood flow;
   b) an elliptical orifice (5) in said wall, said orifice having a length parallel to the longitudinal axis of said incomplete tube, and a width along said circumference, said orifice having an apical end toward the front end and a heel end toward the rear end of said incomplete tube, and a perimeter;
   c) at least one tongue-shaped structure (6,10) projecting from said wall outwardly and rearwardly with respect to the longitudinal axis, adjacent at least one end of said orifice, said structure (6, 10) comprising a base at said one end of the orifice and gradually tapering to a tip at its outer end;
   d) said wall, said orifice, and said tongue-shaped structure having blunt edges and said wall and structure having highly polished internal surfaces; and
   e) said device comprising a stiff or moderately elastic, biologically inert, non-moistenable, non-resorbable, sterilizable material.

2. The device according to claim 1, wherein the length of said incomplete tube is at least five times the diameter of said incomplete tube.

3. The device according to claim 1, wherein the incomplete tube segment comprises approximately two-thirds the circumference of the complete tube.

4. The device according to claim 1, wherein said orifice has a length of at least twice the diameter of said incomplete tube.

5. The device according to claim 1, wherein said orifice has a width of at least one quarter of the circumference of said complete tube.

6. The device according to claim 1, wherein the orifice has a length of about two-fifths of the length of the incomplete tube and is positioned in the wall with its apical end approximately two-fifths of the incomplete tube length from the front end and its heel end approximately one-fifth of the incomplete tube length from the rear end.

7. The device according to claim 1, wherein said at least one tongue-shaped structure projects outwardly at an angle of about 20 to about 45 degrees with respect to the longitudinal axis of said incomplete tube.

8. The device according to claim 1, wherein said at least one tongue-shaped structure has a length between the base and the tip of at least twice the diameter of said incomplete tube.

9. The device according to claim 1, wherein said at least one tongue-shaped structure has a moderately curved shape from its base to its tip, said curved shape being concave facing outwardly.

10. The device according to claim 1, wherein said wall has at least one pair of holes (9) in said wall adjacent said orifice for receiving sutures.

11. The device according to claim 10, wherein said at least one pair of holes (9) includes one hole adjacent each end of the orifice.

12. The device according to claim 10, wherein said at least one pair of holes (9) is located along the perimeter of the orifice intermediate the ends of the orifice.

13. The device according to claim 1, wherein said at least one tongue-shaped structure (10) projects from the heel end of said orifice.

14. The device according to claim 1, wherein said at least one tongue-shaped structure (6) projects from the apical end of said orifice.

15. The device according to claim 1, including two of said tongue-shaped structures (6,10) projecting one from each end of said orifice, wherein said tongue-shaped structures have approximately equal lengths and project from said orifice at an angle of about 20 to about 45 degrees with respect to the longitudinal axis of said incomplete tube.

16. The device according to claim 15, further comprising a pair of holes (12) located one at the tip of each said tongue-shaped structure (6,10).

17. The device according to claim 1, wherein said material is selected from the group consisting of stainless steel, carbon steel, carbon composites, glass and synthetic material.

18. The device according to claim 1, wherein said material is selected from the group consisting of graphite-coated stainless steel and titanium-coated synthetic material.

* * * * *